United States Patent [19]
Dargazanli et al.

[11] Patent Number: 5,922,739
[45] Date of Patent: Jul. 13, 1999

[54] 5-NAPHTHALEN-1-YL-1,3-DIOXANE DERIVATIVES, PREPARATION AND THERAPEUTICAL USE THEREOF

[75] Inventors: Gihad Dargazanli, L'Hay les Roses; Yannick Evanno, Bullion; Jonathan Frost, Wissous; Patrick Lardenois, Bourg la Reine; Mireille Sevrin, Paris; Pascal George, Saint Arnoult en Yvelines, all of France

[73] Assignee: Synthelabo, Le Plessis Robertson, France

[21] Appl. No.: 09/077,710

[22] PCT Filed: Dec. 4, 1996

[86] PCT No.: PCT/FR96/01926

§ 371 Date: Jun. 8, 1998

§ 102(e) Date: Jun. 8, 1998

[87] PCT Pub. No.: WO97/20836

PCT Pub. Date: Jun. 12, 1997

[30] Foreign Application Priority Data

Dec. 6, 1995 [FR] France ................... 95 14394

[51] Int. Cl.⁶ .......................... A01N 43/32; A01N 43/40; C07D 319/06; C07D 401/00
[52] U.S. Cl. ....................... 514/326; 549/373; 548/517; 546/207; 546/245; 514/336; 514/422; 514/452
[58] Field of Search ............. 549/373; 514/452, 514/422, 336, 326; 546/207, 245; 548/517

[56] References Cited

U.S. PATENT DOCUMENTS 5,192,797 3/1993 Raizon et al. .................... 514/452

*Primary Examiner*—John Kight
*Attorney, Agent, or Firm*—Jacobson, Price, Holman & Stern, PLLC

[57] ABSTRACT

Compounds of general formula (I)

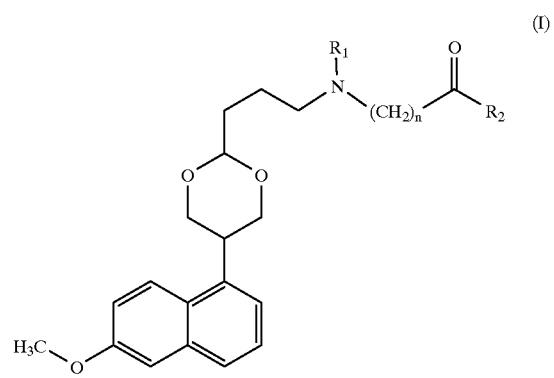

in which $R_1$ represents a hydrogen atom or a $(C_1-C_4)$alkyl, $(C_3-C_6)$cycloalkylmethyl or phenyl-$(C_1-C_3)$alkyl group optionally substituted on the phenyl ring with one or more atoms or groups chosen from halogens and methyl, trifluoromethyl, methoxy and cyano groups, $R_2$ represents a hydroxyl or alkoxy group or a group of general formula $NR_3R_4$ in which $R_3$ and $R_4$ each represent a hydrogen atom, an alkyl group, a cycloalkyl group, a cycloalkylmethyl group, a phenyl group, a phenylmethyl group or a pyridyl group, or alternatively $R_3$ and $R_4$ form, together with the nitrogen atom, a pyrrolidine or piptzidine ring, and n represents the number 1, 2 or 3.

Application in therapy.

9 Claims, No Drawings

5-NAPHTHALEN-1-YL-1,3-DIOXANE DERIVATIVES, PREPARATION AND THERAPEUTICAL USE THEREOF

The present invention relates to compounds of general formula (I)

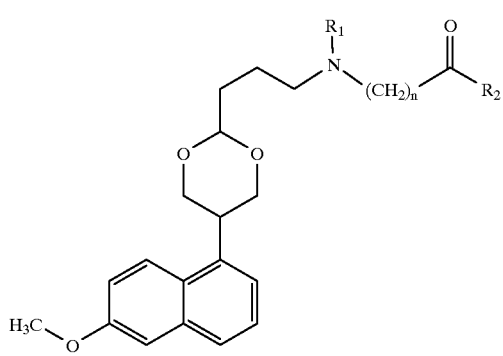

in which $R_1$ represents a hydrogen atom or a $(C_1-C_4)$alkyl, $(C_3-C_6)$cycloalkylmethyl or phenyl$(C_1-C_3)$alkyl group optionally substituted on the phenyl ring with one or more atoms or groups chosen from halogens and methyl, trifluoromethyl, methoxy and cyano groups, $R_2$ represents a hydroxyl or $(C_1-C_4)$alkoxy group or a group of general formula $NR_3R_4$ in which $R_3$ and $R_4$, independently of each other, each represent a hydrogen atom, a linear or optionally branched $(C_1-C_4)$alkyl group, a $(C_3-C_6)$cycloalkyl group, a $(C_3-C_6)$cycloalkylmethyl group, a phenyl group, a phenylmethyl group or a pyridyl group, or alternatively $R_3$ and $R_4$ form, together with the nitrogen atom which bears them, a pyrrolidine or piperidine ring, and n represents the number 1, 2 or 3.

The compounds of the invention may exist in the form of cis or trans stereoisomers or mixtures of such isomers; they may also exist in the form of free bases or addition salts with acids.

The preferred compounds are those of general formula (I) in which $R_1$ represents a methyl, ethyl or phenylmethyl group optionally substituted on the phenyl ring, $R_2$ represents an amino or $(C_1-C_4)$alkylamino group and n is equal to 1; among the latter, the compound in whose formula $R_1$ represents a phenylmethyl group and $R_2$ represents an amino group is particularly advantageous.

The compounds according to the invention may be prepared by various processes.

According to a first variant, an amine of general formula (II)

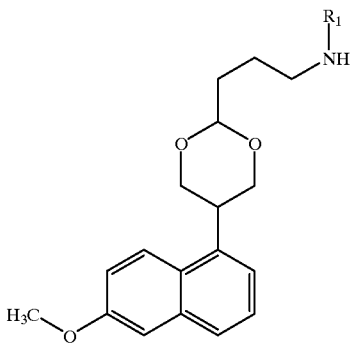

in which $R_1$ represents a hydrogen atom or an alkyl group, may be reacted with an ω-halo alkanoate of general formula (III)

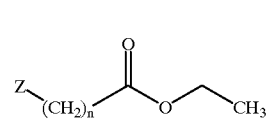

in which Z represents a chlorine or bromine atom and n is as defined above; a compound of general formula (I) is thus obtained in which $R_1$ represents a hydrogen atom or an alkyl group and $R_2$ represents an ethoxy group. If so desired, the compound thus obtained may then be saponified to convert it into the corresponding acid, or alternatively it may be reacted with an amine of general formula $HNR_3R_4$, in which $R_3$ and $R_4$ are as defined above, to convert it into amide. The conditions of these reactions are standard and are well known to those skilled in the art.

According to a second variant, the amides of general formula (I) in which $R_1$ represents a hydrogen atom or an alkyl group may be obtained by reacting the amine of general formula (II) directly with an ω-halo alkanamide of general formula (IV)

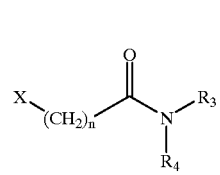

in which X represents a chlorine or bromine atom and $R_3$, $R_4$ and n are as defined above. The conditions of this reaction are well known to those skilled in the art.

According to a third variant, the amides of general formula (I) in which $R_1$ represents a hydrogen atom or an alkyl group and n=2 may be obtained by reacting the amine of general formula (II) with a propenamide of general formula (V)

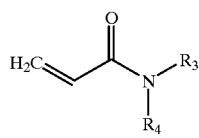

(V)

in which R₃ and R₄ are as defined above. The conditions of this Michael reaction are well known.

Lastly, and according to a fourth variant, the compounds of general formula (I) in which $R_1$ does not represent a hydrogen atom may be prepared by alkylation of the corresponding compound in whose formula $R_1$ represents a hydrogen atom, in a polar aprotic solvent, for example acetonitrile, in the presence of a base, for example potassium carbonate.

The starting amines of general formula (II) in which $R_1$ represents an alkyl group may be obtained by reduction of the corresponding alkanamides, described in Patent Application EP-461,958; the starting amines of general formula (II) in which $R_1$ represents a hydrogen atom may be obtained by reaction of 2-(6-methoxynaphthalen-1-yl)propane-1,3-diol with 4,4-diethoxybutanamine, as described in the said patent application.

The starting compounds of general formulae (III), (IV) and (V) are commercially available or may be obtained by known methods.

The examples which follow illustrate the preparation of a few compounds of the invention. The elemental microanalyses and the IR and NMR spectra confirm the structures of the compounds obtained.

The numbers indicated in parentheses in the titles of the examples correspond to those of the 1st column of Table 1 given later.

In the compound names, the hyphen "-" forms part of the name, and the underscore "_" serves only as a line-break hyphen; it should be removed in the absence of a line-break, and should not be replaced by either a normal hyphen or a space.

EXAMPLE 1

(Compound No. 1).

2- [[3- [5- (6-Methoxynaphthalen-1-yl) -1,3-dioxan-2-yl] propyl]amino]acetamide.

1.1. 5-(6-Methoxynaphthalen-1-yl)-1,3-dioxane-2-propanamine hydrochloride.

7.56 g (32.5 mmol) of 2-(6-methoxynaphthalen-1-yl) propane-1,3-diol, 6.8 g (42.1 mmol) of 4,4-diethoxybutanamine and then 70 ml of hydrochloric ether are introduced into a 1 l round-bottomed flask containing 300 ml of toluene and the mixture is heated at reflux for 2 h.

The mixture is cooled and the precipitate is collected by filtration and rinsed with diethyl ether.

10.2 g of crude hydrochloride are obtained in the form of a beige-coloured solid.

Melting point: 224–226° C. 1.2. 2-[[3-[5-(6-Methoxynaphthalen-l-yl)-1,3-diox_an-2-yl]propyl]amino] acetamide.

1.2 g (4 mmol) of 5-(6-methoxynaphthalen-1-yl)-1,3-dioxane-2-propanamine, 0.8 g (5.8 mmol) of potassium carbonate and 0.4 g (4.2 mmol) of chloroacetamide are introduced into a 100 ml round-bottomed flask containing 30 ml of acetonitrile and the mixture is heated at 80° C. for 3 h.

The mixture is allowed to cool, 50 ml of water are added and the resulting mixture is extracted with twice 50 ml of ethyl acetate. The organic phase is washed with water and dried over magnesium sulphate, the solvent is evaporated off under reduced pressure and the residue is purified by chromatography on a column of silica gel, eluting with a ⁹⁵⁄₅ mixture of dichloromethane and methanol.

0.4 g (1.1 umol) of white solid is obtained, which is recrystallized from ethanol.

Melting point: 148–150° C.

EXAMPLE 2

(Compound No. 6).

2-[Ethyl[3-[5-(6-methoxynaphthalen-1-yl)-1,3-dioxan-2-yl] propyl]amino]acetamide.

2.1. N-Ethyl-5-(6-methoxynaphthalen-1-yl)-1,3-dioxane-2-propanamine hydrochloride.

A suspension of 10 g (29.1 mmol) of N-[3-[5-(6-methoxynaphthalen-1-yl)-1,3-dioxan-2-yl]propyl]acet_amide in 75 ml of tetrahydrofuran is added to a 500 ml round-bottomed flask containing a suspension of 1.66 g (43.6 mmol) of lithium aluminium hydride in 50 ml of tetrahydrofuran heated to reflux, and the refluxing and stirring are maintained for 3 h.

The mixture is cooled and hydrolysed by adding 10.5 ml of 1M sodium potassium tartrate solution, it is stirred for 12 h, the solid is separated out by filtration, by washing the latter with tetrahydrofuran, and the filtrate is concentrated to dryness under reduced pressure.

10.27 g of oily product are obtained, 0.5 g of which is taken to form the hydrochloride from ethanol.

Melting point: 165° C. (decomposition).

2.2. 2- [thyl[3-[5-(6-methoxynaphthalen-1-yl)-1,3-di_oxan-2 -yl] propyl] amino] acetamide.

3 g (8.2 nmol) of N-ethyl-5-(6-methoxy_naphthalen-1-yl) -1,3 -dioxane-2 -propanamine hydrochloride, 5.6 g (40.5 mmol) of potassium carbonate and 0.9 g (9.6 mmol) of chloroacetamide are introduced into a 100 ml round-bottomed flask containing 40 ml of N,N-dimethylformamide, and the mixture is heated at 80° C. for 4 h.

The mixture is allowed to cool, 70 ml of water are added and the resulting mixture is extracted with twice 100 ml of ethyl acetate. The organic phase is washed with water, dried over magnesium sulphate and filtered, the solvent is evaporated off under reduced pressure and the residue is purified by chromatography on a column of silica gel, eluting with a ⁹⁸⁄₂ mixture of dichloromethane and methanol.

2.6 g (6.7 mmol) of white solid are obtained, which product is recrystallized from a mixture of isopropyl ether and dichloromethane.

Melting point: 120–121° C.

EXAMPLE 3

(Compound No. 10).

2-[Ethyl[3-[5-(6-methoxynaphthalen-1-yl)-1,3-dioxan-2-yl] propyl]amino]-N-pyrid-2-ylacetamide (E)-but-2-ene_dioate (1:1).

1.4 g (4.24 mmol) of N-ethyl-S-(6-methoxy_naphthalen-1-yl)-1,3-dioxane-2-propanamine, 0.6 g (4.3 mmol) of potassium carbonate and 0.72 g (4.2 mmol) of 2-chloro-N-pyrid-2-ylacetamide are introduced into a 100 ml round-bottomed flask containing 25 ml of acetonitrile, and the mixture is stirred at 25° C. for 12 h.

50 ml of water are added and the resulting mixture is extracted with twice 50 ml of ethyl acetate. The organic phase is washed with water, dried over magnesium sulphate and filtered, the solvent is evaporated off under reduced pressure and the residue is purified by chromatography on a column of silica gel, eluting with a ⁷⁰⁄₃₀ mixture of petroleum ether and ethyl acetate. 1.46 g (3.15 mmol) of compound are obtained, which product is crystallized in the form of the fumarate from isopropyl ether.
Melting point: 60–67° C.

EXAMPLE 4
(Compound No. 17).
3-(Ethyl[3-(5-(6-methoxynaphthalen-1-yl)-1,3-dioxan-2-yl]propyl]amino]propanamide ethanedioate (1:1).

1.3 g (4 mmol) of N-ethyl-5-(6-methoxynaph_thalen-1-yl)-1,3-dioxane-2-propanamine and 0.43 g (6 mmol) of acrylamide are introduced into a 100 ml round-bottomed flask containing 20 ml of acetonitrile, and the mixture is heated at reflux for 8 h. A further 0.3 g (4 mmol) of acrylamide is added and the refluxing is maintained for an additional 8 h. The mixture is cooled and concentrated to dryness under reduced pressure and the residue is taken up in 50 ml of water and extracted with twice 50 ml of ethyl acetate. The organic phase is washed with water, dried over magnesium sulphate and filtered, the solvent is evaporated off under reduced pressure and the residue is purified by chromatography on a column of silica gel, eluting with a $97/3$ mixture of dichloromethane and methanol.

0.98 g of compound is obtained, which is crystallized in the form of the oxalate from 2-propanol.
Melting point: 125° C. (decomposition).

EXAMPLE 5
(Compound No. 7).
2-[Ethyl[3-[5-(6-methoxynaphthalen-1-yl)-1,3-dioxan-2-yl]propyl]amino]-N-methylacetamide ethanedioate (1:1). 5.1. Ethyl 2-[ethyl(3-[5-(6-methoxynaphthalen-1-yl)- 1,3-dioxan-2-yl)propyl)amino)acetate.

1.4 g (4.24 mmol) of N-ethyl-5-(6-methoxy_napthalen-1-yl)-1,3-dioxane-2-propanamine, 1.75 g (12.7 mmol) of potassium carbonate and 0.5 ml (4.45 mmol) of ethyl bromoacetate are introduced into a 100 ml round-bottomed flask containing 21 ml of acetonitrile, and the mixture is heated at reflux for 2 h.

The mixture is cooled and concentrated to dryness under reduced pressure and the residue is taken up in 50 ml of water and extracted with twice 50 ml of ethyl acetate. The organic phase is washed with water, dried over magnesium sulphate and filtered and the solvent is evaporated off under reduced pressure. The residue is purified by chromatography on a column of silica gel, eluting with a $99/1$ mixture of dichloromethane and methanol, and 1.17 g (3 mmol) of compound are obtained in the form of a colourless oil. The oxalate is prepared therefrom in a conventional manner.
Melting point: 124–127° C.
5.2. 2-[Ethyl[3-[5-(6-methoxynaphthalen-1-yl)-1,3-dioxan-2-yl]propyl]amino]-N-methylacetamide ethanedioate (1:1).

1.15 g (3 mmol) of ethyl 2-[ethyl[3-[5-(6-methoxynaphthalen-1-yl)-1,3-dioxan-2-yl]propyl]amino)_acetate are introduced into a 250 ml reactor containing 11 ml of a 33% solution of methylamine in ethanol, and the sealed mixture is heated at 50° C. for 5 days.

The mixture is cooled and concentrated to dryness under reduced pressure and the residue is taken up in 50 ml of water and extracted with twice 50 ml of ethyl acetate. The organic phase is washed with water, dried over magnesium sulphate and filtered and the solvent is evaporated off under reduced pressure. 1.16 g (2.89 mmol) of compound are obtained in the form of a yellow oil which is crystallized in the form of the oxalate from 2-propanol.
Melting point: 140° C. (decomposition).

EXAMPLE 6
(Compound No. 18).
Ethyl 4-[ethyl[3-[5-(6-methoxynaphthalen-1-yl)-1,3-dioxan-2-yl]propyl]amino]butanoate ethanedioate.

7.31 g (20 mmol) of N-ethyl-5-(6-methoxy_naphthalen-1-yl)-1,3-dioxane-2-propanamine hydrochloride, 2.76 g (20 mmol) of potassium carbonate and 3.9 g (20 mmol) of ethyl bromobutanoate are introduced into a 100 ml round-bottomed flask containing 50 ml of N,N-dimethylformamide, and the mixture is heated at 80° C. for 7 h.

The mixture is allowed to cool and is concentrated to dryness under reduced pressure, the residue is taken up in 70 ml of water and extracted with twice 100 ml of ethyl acetate, the organic phase is washed with water, dried over magnesium sulphate and filtered, the solvent is evaporated off under reduced pressure and the residue is purified by chromatography on a column of silica gel, eluting with a $90/10$ mixture of dichloromethane and methanol.

6.1 g (13.7 mmol) of oily compound are obtained, which product is crystallized in the form of the oxalate from ethyl acetate.
Melting point: 132–135° C.

EXAMPLE 7
(Compound No. 15).
2-[[3-[S-(6-Methoxynaphthalen-1-yl)-1,3-dioxan-2-yl]_propyl](phenylmethyl)amino]acetamide hydrochloride.

0.5 g (1.39 mmol) of 2-[[3-[5-(6-methoxy_naphthalen-1-yl)-1,3-dioxan-2-yl]propyl]amino]acet_amide, 0.29 g (2.1 mmol) of potassium carbonate and 0.18 ml (1.5 mmol) of benzyl bromide are introduced into a 25 ml round-bottomed flask containing 8 ml of acetonitrile, and the mixture is heated at reflux for 2 h.

The mixture is allowed to cool, 15 ml of water are added, the resulting mixture is extracted with twice 15 ml of ethyl acetate, the organic phase is washed with water, dried over magnesium sulphate and filtered, the solvent is evaporated off under reduced pressure and the residue is purified by chromatography on a column of silica gel, eluting with a $98/2$ mixture of dichloromethane and methanol.

0.24 g (0.53 mmol) of compound is obtained in the form of an oil, which is crystallized in the form of the hydrochloride from isopropyl ether.
Melting point: 218–220° C.

EXAMPLE 8
(Compound No. 21).
2-[Ethyl[3-[5-(6-methoxynaphthalen-1-yl)-1,3-dioxan-2-yl]propyl]amino]-N-(1-methylethyl)acetamide ethane_dioate (1:1).

0.23 ml (2.73 mmol) of 1-methylethylamine, 0.38 ml (2.73 mmol) of triethylamine and then a solution of 0.22 ml (2.73 mmol) of chloroacetyl chloride in 10 ml of dioxane are introduced, under an inert atmosphere, into a 250 ml round-bottomed flask containing 20 ml of dioxane, and the mixture is left stirring for 15 h.

30 ml of water, then 1 g (7.23 mmol) of potassium carbonate and then 1 g (2.73 mmol) of N- ethyl-5-(6-methoxynaphthalen-1-yl)-1,3-dioxane-2-propanamine hydrochloride are added and the mixture is heated at 80° C. for 7 h.

The mixture is cooled, 80 ml of water are added, the resulting mixture is extracted with twice 50 ml of ethyl acetate, the organic phase is washed with water, dried over magnesium sulphate and filtered and the solvent is evaporated off under reduced pressure. The product obtained is purified by chromatography on a column of silica gel, eluting with a 95/5 mixture of dichloromethane and methanol, and 0.8 g (1.86 mmol) of compound is obtained in the form of a colourless oil.

The oxalate is prepared therefrom in a conventional manner.

Melting point: 130–131° C.

EXAMPLE 9

(Compound No. 37)

2-[[(2-Fluorophenyl)methyl][3-[5-(6-methoxynaphthalen-1-yl)-1,3-dioxan-2-yl]propyllamino]acetamide hydrochloride (1:1).

1 g (2.79 mmol) of 2-[[3-[5-(6-methoxynaph_thalen-1-yl)-1,3-dioxan-2-yl]propyl] amino]acetamide, 0.8 g (578 mmol) of potassium carbonate and 0.5 ml (4.2 mmol) of 1-(chloromethyl)-2-fluorobenzene are introduced into a 100 ml round-bottomed flask containing 20 ml of acetonitrile, and the mixture is heated at reflux for 6 h.

The mixture is allowed to cool, 30 ml of water are added and the resulting mixture is extracted with twice 20 ml of ethyl acetate. The organic phase is washed with water, dried over magnesium sulphate and filtered and the solvent is evaporated off under reduced pressure. The product obtained is purified by chromatography on a column of silica gel, eluting with a 98/2 mixture of dichloromethane and methanol.

0.34 g (0.73 mmol) of compound is obtained in the form of a colourless oil, which is crystallized in the form of the hydrochloride from 2-propanol.

Melting point: 200–202° C.

EXAMPLE 10

(Compound No. 30).

2-[(Cyclopropylmethyl,[3-[5-(6-methoxynaphthalen-1-yl)-1,3-dioxan-2-yl]propyl]amino]actamide (E)-2-butene_dioate (1:1)

1 g (2.79 mzol) of 2-[[3-[5-(6-methoxynaph_thalen-1-yl) -1, 3-dioxan-2-yl]propyl] amino] acetamide, 0.8 g (5.78 mmol) of potassium carbonate, 0.38 g (4.2 mmol) of (chloromethyl)cyclopropane and a catalytic amount of sodium iodide are introduced into a 250 ml round-bottomed flask containing 15 ml of N,N-dimethylformamide, and the mixture is heated at 100° C. for 20 h.

The mixture is allowed to cool, the solvent is evaporated off under reduced pressure, the residue is taken up in dichloromethane, the insoluble material is separated out by filtration, the filtrate is concentrated to dryness under reduced pressure and the product obtained is purified by chromatography on a column of silica gel, eluting with a 9/1 mixture of dichloromethane and methanol. 0.60 g (1.45 mmol) of compound is obtained in the form of a colourless oil, which is crystallized in the form of the fumarate from 2-propanol.

Melting point: 149–150° C.

EXAMPLE 11

(Compound No. 41).

Ethyl 2-[[3-[5-(6-Methoxynaphthalen-1-yl)-1,3-dioxan-2-yl]propyll(phenylmethyl)amino)acetate.

11.1 Ethyl 2-[[3-[5-(6-methoxynaphthalen-1-yl)-1,3-dioxan-2-yl]propyl] amino] acetate.

6.64 g (22 mmol) of 5-(6-me-hoxynaphthalen-1-yl)-1,3-dioxane-2-propanamine, 3 g (22 mnol) of potassium carbonate and 3.54 ml (33 mmol) of ethyl chloroacetate are introduced into a 50 ml round-bottomed flask containing 110 ml of N,N-dimethyl_formamide, and the mixture is heated at 80° C. for 20 min.

The mixture is allowed to cool, the solvent is evaporated off under reduced pressure and the residue is taken up in 50 ml of water and is extracted with twice 50 ml of ethyl acetate. The organic phase is washed with water, dried over magnesium sulphate and filtered, the filtrate is concentrated to dryness under reduced pressure and the product obtained is purified by chromatography on a column of silica gel, eluting with a 98/2 mixture of dichloromethane and methanol.

3.52 g (9.08 mmol) of compound are obtained in the form of a colourless oil, which is used without further purification in the following step. 11.2 Ethyl 2-[[3-[5-(6-methoxynaphthalen-1-yl)-1,3-dioxan-2-yl]propyl] (phenylmethyl)amino]acetate.

3.52 g (9.08 mmol) of ethyl 2-[[3-[5-(6-methoxynaphthalen-1-yl)-1,3-dioxan-2-yl]propyl]$_{13}$ amino]acetate, 1.2 g of potassium carbonate and 1.05 ml (9.12 mmol) of (chloromethyl)benzene are introduced into a 250 ml round-bottomed flask containing 45 ml of acetonitrile, and the mixture is heated at 80*C for 6 h.

The mixture is allowed to cool and is concentrated to dryness under reduced pressure, the residue is taken up in 50 ml of water and extracted with twice 50 ml of ethyl acetate, the organic phase is washed with water, dried over magnesium sulphate and filtered and the solvent is evaporated off under reduced pressure. 3.7 g of oily product are obtained, 1 g of which is purified by chromatography on a column of silica gel, eluting with a 99/1 mixture of dichloromethane and methanol.

0.5 g (2.09 mmol) of compound is obtained in the form of a colourless oil, which is crystallized from diisopropyl ether.

Melting point: 58–60° C.

EXAMPLE 12

(Compound No. 39).

2-[[3- [5- (6-Methoxynaphthalen-1-yl) -1,3-dioxan-2-yl] propyl] (phenylmethyl) amino] -N-methylacetamide hydrochloride (1:1).

1 g (2.15 mmol) of ethyl 2-[[3-[S-(6-methoxynaphthalen-1-yl)-1,3-dioxan-2-yl]propyl]_(phenylmethyl)amino] acetate is introduced into a 250 ml reactor containing 8 ml of a 33% solution of methylamine in ethanol, and the sealed mixture is heated at 50° C. for 3 days.

The mixture is allowed to cool and is concentrated to dryness under reduced pressure, the residue is taken up in 50 ml of water and extracted with twice 50 ml of ethyl acetate, the organic phase is washed with water, dried over magnesium sulphate and filtered and the solvent is evaporated off under reduced pressure. The product obtained is purified by chromatography on a column of silica gel, eluting with a 98/2 mixture of dichloromethane and methanol.

0.51 g (1.1 mmol) of compound is obtained in the form of a colourless oil, which is crystallized in the form of the hydrochloride from duisopropyl ether.

Melting point: 98–100° C.

The table which follows illustrates the chemical structures and the physical properties of a few compounds according to the invention.

TABLE

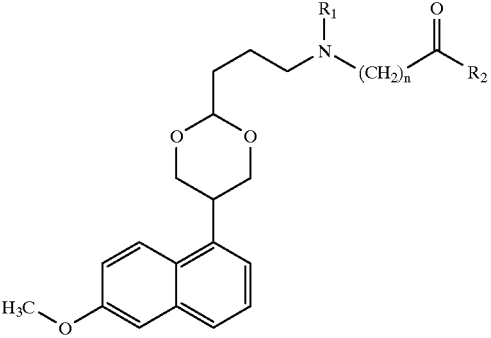

| No. | $R_1$ | $R_2$ | n | Salt | m.p. (° C.) or $n_D^{20}$ |
|---|---|---|---|---|---|
| 1 | H | $NH_2$ | 1 | — | 148–150 |
| 2 | $CH_3$ | $OCH_2CH_3$ | 1 | ox. (1:1) | 127–128 |
| 3 | $CH_3$ | $NH_2$ | 1 | — | 146–147 |
| 4 | $CH_3$ | $NHCH_3$ | 1 | — | 106–107 |
|   |   |   |   | ox. (1:1) | 169–170 |
| 5 | $CH_2CH_3$ | $OCH_2CH_3$ | 1 | ox. (1:1) | 124–127 |
| 6 | $CH_2CH_3$ | $NH_2$ | 1 | — | 120–121 |
| 7 | $CH_2CH_3$ | $NHCH_3$ | 1 | ox. (1:1) | 140 (d) |
| 8 | $CH_2CH_3$ | $NHC_6H_5$ | 1 | ox. (1:1) | 168–169 |
|   |   |   |   | fum. (1:1) | 70–72 |
| 9 | $CH_2CH_3$ | $NHCH_2C_6H_5$ | 1 | ox. (1:1) | 145–146 |
| 10 | $CH_2CH_3$ | $NH-2-NC_5H_4$ | 1 | fum. (1:1) | 60–67 |
| 11 | $CH_2CH_3$ | $NHC_6H_{11}$ | 1 | — | 102–103 |
| 12 | $CH_2CH_3$ | $NC_5H_{10}$ | 1 | — | $n_D^{20} = 1.571$ |
| 13 | $CH_2CH_3$ | $NC_4H_8$ | 1 | — | $n_D^{20} = 1.573$ |
| 14 | $CH_2CH_3$ | $NHCH_2CH(CH_3)_2$ | 1 | ox. (1:1) | 136–137 |
| 15 | $CH_2C_6H_5$ | $NH_2$ | 1 | HCl (1:1) | 218–220 |
| 16 | H | $NH_2$ | 2 | — | 122 (d) |
| 17 | $CH_2CH_3$ | $NH_2$ | 2 | ox. (1:1) | 125 (d) |
| 18 | $CH_2CH_3$ | $OCH_2CH_3$ | 3 | ox. (1:1) | 132–135 |
| 19 | $CH_2CH_3$ | $NH_2$ | 3 | — | 89–90 |
| 20 | $CH_2CH_3$ | $NHCH_3$ | 3 | — | $n_D^{20} = 1.571$ |
| 21 | $CH_2CH_3$ | $NHCH_3$ | 1 | ox. (1:1) | 130–131 |
| 22 | $CH_2CH_3$ | $NHCH_2C_3H_5$ | 1 | ox. (1:1) | 126–127 |
| 23 | $CH_3$ | $NH_2$ | 2 | ox. (1:1) | 137 (d) |
| 24 | $CH_2CH_3$ | OH | 3 | — | 50–60 |
| 25 | $CH_2C_6H_4$-4-$CH_3$ | $NH_2$ | 1 | HCl (1:1) | 194 (d) |
| 26 | $CH_2C_6H_4$-3-$CH_3$ | $NH_2$ | 1 | — | 132–133 |
| 27 | $CH_2C_6H_4$-4-$OCH_3$ | $NH_2$ | 1 | HCl (1.1:1) | 160 (d) |
| 28 | $CH_2C_6H_4$-3-Cl | $NH_2$ | 1 | HCl (1:1) | 178 (d) |
| 29 | $CH_2C_6H_4$-4-Br | $NH_2$ | 1 | HCl (1.2:1) | 189–191 |
| 30 | $CH_2C_3H_5$ | $NH_2$ | 1 | fum. (1:1) | 149–150 |
| 31 | $CH_2C_6H_4$-3-$CF_3$ | $NH_2$ | 1 | fum. (1:1) | 168–169 |
| 32 | $CH_2C_6H_4$-4-Cl | $NH_2$ | 1 | HCl (1.1:1) | 160–162 |
| 33 | $CH_2C_6H_{11}$ | $NH_2$ | 1 | HCl (1:1) | 163–165 |
| 34 | $CH_2C_6H_4$-2-Cl | $NH_2$ | 1 | — | 117–118 |
| 35 | $CH_2C_6H_4$-3-$OCH_3$ | $NH_2$ | 1 | — | 107–108 |
| 36 | $CH_2C_6H_4$-3-F | $NH_2$ | 1 | HCl (1:1) | 160–162 |
| 37 | $CH_2C_6H_4$-2-F | $NH_2$ | 1 | HCl (1:1) | 200–202 |
| 38 | $(CH_2)_2C_6H_5$ | $NH_2$ | 1 | HCl (1:1) | 55 (d) |
| 39 | $CH_2C_6H_5$ | $NHCH_3$ | 1 | HCl (1:1) | 98–100 |
| 40 | $CH_2C_6H_4$-2-$CH_3$ | $NH_2$ | 1 | HCl (0.7:1) | 187–189 |
| 41 | $CH_2C_6H_5$ | $OCH_2CH_3$ | 1 | — | 58–60 |
| 42 | $CH_2C_6H_4$-4-F | $NH_2$ | 1 | HCl (1:1) | 138–140 |
| 43 | $CH_2C_6H_5$ | $NHCH_2CH_3$ | 1 | HCl (1:1) | 70–72 |
| 44 | $CH_2C_6H_4$-2-$OCH_3$ | $NH_2$ | 1 | fum. (1:1) | 173–174 |
| 45 | $(CH_2)_3C_6H_5$ | $NH_2$ | 1 | HCl (1.1:1) | 150 (d) |
| 46 | $CH_2C_6H_4$-3-CN | $NH_2$ | 1 | fum. (1.1:1) | 163–165 |

In the "$R_1$" and "$R_2$" columns, $C_3H_5$ represents a cyclopropyl group, $C_6H_{11}$ represents a cyclohexyl group, $C_6H_5$ represents a phenyl group, $C_6H_4$-p-Y represents a phenyl group bearing a substituent Y in the para position, 2-$NC_5H_4$ represents a 2-pyridyl group, $NC_4H_8$ represents a 1-pyrrolidinyl group ard $NC_5H_{10}$ represents a 1-piperidyl group.

In the "Salt" column, "-" denotes a compound in the form of the base, "ox." denotes an oxalate (or ethanedioate), "fum." denotes a fumarate (or (E)-2-butenedioate) and "HCl" denotes a hydrochloride; the acid:base molar ratio is indicated in parentheses.

In the final column, the melting points m.p. (°C) or the refractive indices $n_D^{20}$ are indicated; "(d)" denotes a melting point with decomposition.

All the compounds are trans stereoisomers ($^1$H NMR), except for compound No. 24 which is a predominantly trans mixture of cis and trans stereoisomers.

The compounds according to the invention underwent pharmacological tests which demonstrated their value as therapeutic substances.

Neuroprotective activity with respect to focal ischaemia in rats.

The neuroprotective activity of compounds according to the invention was demonstrated in a model of permanent focal ischaemia brought about by intraluminal occlusion of the middle cerebral artery in rats, according to a method similar to that described in Stroke (1989) 20 84–91.

Under anaesthesia with methohexital sodium, the pterygopalatine artery, the common carotid artery and the left outer carotid artery are ligated and a nylon thread is introduced into the inner carotid artery over a length of about 18 mm, corresponding to the distance which separates the origin of the inner carotid artery from that of the middle cerebral artery.

The test compounds are administered after intravenous occlusion.

24 hours after occlusion of the middle cerebral artery, the animals are sacrificed and the brain is removed.

The volume of the cerebral infarct is evaluated by measuring the surface area of the necrosis on 6 coronal slices stained with 2,3,5-triphenyltetrazolium chloride. By way of example, compounds No. 6 and No. 15 in the preceding table significantly reduce the volume of the infarct, by about 31% and 50% respectively, at a dose of 3 mg/kg administered intravenously at times 10 min, 1 h 30 min, 3 h and 6 h after the occlusion.

Activity towards tonic convulsions introduced in mice by a supramaximal electric shock.

The procedure of this test is described by E. A. Swinyard and J. H. Woodhead in *Antiepileptic Drugs,* Raven Press, New York, 111–126 (1982).

10 min after intravenous administration of the test compound, the number of mice exhibiting tonic convulsions (extension of the fore- and hind limbs), immediately after application of an electric current (0.4 s, 60 mA, 50 Hz) using an Apelex ETC UNIT 7801™ machine, is noted. The results are expressed in terms of the $DA_{50}$, the dose which protects 50% of the animals, calculated according to the method of J. T. Lichtfield and F. Wilcoxon (*J. Pharm. Exp. Ther.,* 96, 99–113 (1949)) using the Probit™ program, from 3 or 4 doses each administered to a group of 8 mice. In this test, the $DA_{50}$ values of the compounds of the invention lie between 0.5 and 10 mg/kg.

The results of the tests show that the compounds according to the invention have neuroprotective properties, and that they may thus be used for the preparation of medicaments which are useful in the treatment or prevention of cerebrovascular disorders of ischaemic or hypoxic origin (cerebral infarct, cranial or medullary trauma, cardiac or respiratory arrest, transitory ischaemic attack, perinatal asphyxia), glaucoma, progressive neurodegenerative diseases (senile dementias such as Alzheimer's disease, vascular dementias, Parkinson's disease, Huntington's disease, olivopontocerebellar atrophy, amyotrophic lateral sclerosis, neurodegenerative diseases of viral origin, etc.) and in the prevention of cerebral ischaemic accidents associated with vascular and heart surgery and with endovascular therapy.

On account of their anticonvulsant properties, they may also be used in the treatment of epilepsy. Lastly, the treatment of other complaints, such as neuropathies, neurogenic pains (for example those associated with neuropathies or with migraines), neurological spasticity and dyskinesias, may also be envisaged.

To this end, they may be in all forms of pharmaceutical compositions which are suitable for enteral or parenteral administration, such as tablets, sugar-coated tablets, gelatin capsules, wafer capsules, drinkable or injectable suspensions or solutions such as syrups or ampules, etc., combined with suitable excipients, and dosed to allow a daily administration of from 0 to 1000 mg of active substance.

We claim:

1. Compound, in the form of a pure stereoisomer or a mixture of stereoisomers, corresponding to the general formula (I)

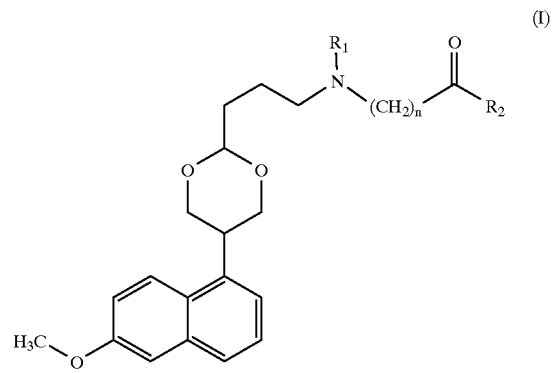

in which $R_1$ represents a hydrogen atom or a ($C_1$–$C_4$)alkyl, ($C_3$–$C_6$)cycloalkylmethyl or phenyl($C_1$–$C_3$)alkyl group optionally substituted on the phenyl ring with one or more atoms or groups chosen from halogens and methyl, trifluoromethyl, methoxy and cyano groups, $R_2$ represents a hydroxyl or ($C_1$–$C_4$)alkoxy group or a group of general formula $NR_3R_4$ in which $R_3$ and $R_4$, independently of each other, each represent a hydrogen atom, a linear or optionally branched ($C_1$–$C_4$)alkyl group, a ($C_3$–$C_6$)cycloalkyl group, a ($C_3$–$C_6$)cycloalkylmethyl group, a phenyl group, a phenylmethyl group or a pyridyl group, or alternatively $R_3$ and $R_4$ form, together with the nitrogen atom which bears them, a pyrrolidine or piperidine ring, and n represents the number 1, 2 or 3, in the form of the free base or an addition salt with an acid.

2. Compound according to claim 1, characterized in that $R_1$ represents a methyl, ethyl or phenylmethyl group optionally substituted on the phenyl ring, $R_2$ represents an amino or ($C_1$–$C_4$)alkylamino group and n is equal to 1.

3. Compound according to claim 1, characterized in that $R_1$ represents a phenylmethyl group, $R_2$ represents an amino group and n is equal to 1.

4. Process for the preparation of compounds according to claim 1, characterized in that an amine of general formula (II)

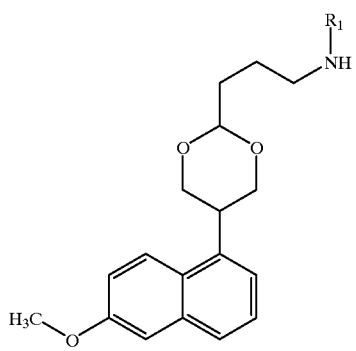
(II)

in which $R_1$ represents a hydrogen atom or an alkyl group, is reacted with an ω-halo alkanoate of general is formula (III)

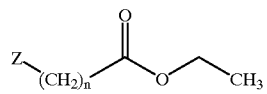
(III)

in which Z represents a chlorine or bromine atom and n is as defined in claim 1, to obtain a compound of general formula (I) in which $R_1$ represents a hydrogen atom or an alkyl group and $R_2$ represents an ethoxy group, then, if so desired, the compound thus obtained is saponified to convert it into the corresponding acid, or alternatively it is reacted with an amine of general formula $HNR_3R_4$, in which $R_3$ and $R_4$ are as defined in claim 1, to convert it into amide.

5. Process for the preparation of compounds according to claim 1, characterized in that an amine of general formula (II)

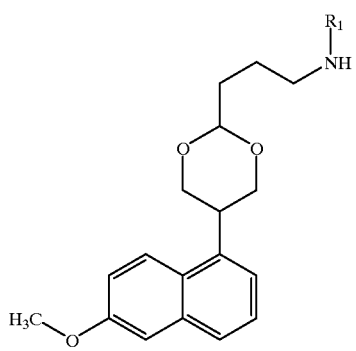
(II)

in which $R_1$ represents a hydrogen atom or an alkyl group, is reacted with an ω-halo alkanamide of general formula (IV)

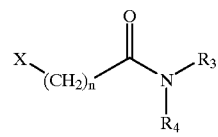
(IV)

in which X represents a chlorine or bromine atom and $R_3$, $R_4$ and n are as defined in claim 1.

6. Process for the preparation of compounds according to claim 1, characterized in that an amine of general formula (II)

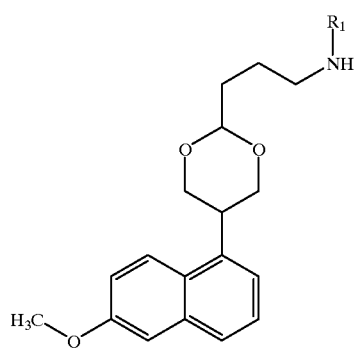
(II)

in which $R_1$ represents a hydrogen atom or an alkyl group, is reacted with a propenamide of general formula (V)

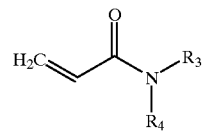
(V)

in which $R_3$ and $R_4$ are as defined in claim 1.

7. Process for the preparation of compounds according to claim 1, characterized in that an alkylation is carried out on a compound of general formula (I) in which $R_1$ represents a hydrogen atom.

8. Medicament, characterized in that it consists of a compound according to claim 1.

9. Pharmaceutical composition, characterized in that it contains a compound according to claim 1, combined with an excipient.

* * * * *